United States Patent

Ribault et al.

(10) Patent No.: US 8,148,081 B2
(45) Date of Patent: Apr. 3, 2012

(54) METHOD FOR DETECTING MICROORGANISMS ON A MEMBRANE

(75) Inventors: Sebastien Ribault, Lingolsheim (FR); Frederic Marc, Itterswiller (FR)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 12/692,741

(22) Filed: Jan. 25, 2010

(65) Prior Publication Data

US 2010/0255476 A1    Oct. 7, 2010

Related U.S. Application Data

(62) Division of application No. 11/638,745, filed on Dec. 14, 2006.

(30) Foreign Application Priority Data

Dec. 20, 2005 (FR) ..................... 05 12971

(51) Int. Cl.
*C12Q 1/68* (2006.01)
*G01N 1/30* (2006.01)
*C07H 21/04* (2006.01)

(52) U.S. Cl. ..................... 435/6.15; 435/6.11; 435/40.5; 536/24.32

(58) Field of Classification Search .................. None
See application file for complete search history.

(56) References Cited

U.S. PATENT DOCUMENTS

| 3,249,572 | A | 5/1966 | Davis et al. |
| 4,871,461 | A | 10/1989 | Karakane et al. |
| 4,941,991 | A | 7/1990 | Rajamannan et al. |
| 6,162,448 | A | 12/2000 | Nguyen et al. |
| 6,551,795 | B1 | 4/2003 | Rubenfield et al. |
| 7,019,113 | B2 | 3/2006 | Rozema et al. |
| 2001/0031498 | A1 | 10/2001 | Leclercq et al. |

FOREIGN PATENT DOCUMENTS

| EP | 0 880 963 A2 | 12/1998 |
| EP | 1464710 A2 | 10/2004 |
| JP | 63-305904 A | 12/1988 |
| JP | 03-218766 A | 9/1991 |
| WO | 01/16363 A2 | 3/2001 |
| WO | 01/59157 A2 | 8/2001 |
| WO | 03/054162 A2 | 7/2003 |
| WO | 2004/050902 A1 | 6/2004 |

OTHER PUBLICATIONS

Wikipedia entry for the topic "Cell Wall", retrieved Sep. 23, 2010 (10 pages).*

Enzyme and Microbial Technology 37 (2005) 300-308; M.Canovas et al.; "Permeabilization of *Escherichia coli* cells in the biotransformation of trimethylammonium compounds into L-Carnitine".

(Continued)

*Primary Examiner* — Diana Johannsen
(74) *Attorney, Agent, or Firm* — Nields, Lemack & Frame, LLC (57) ABSTRACT

The present invention relates to a method using a composition for permeabilizing microorganism walls for counting and detecting in a targeted manner the microorganisms on a membrane. The invention also relates to a kit and to probes that are suitable for carrying out the method.

12 Claims, 8 Drawing Sheets

OTHER PUBLICATIONS

Microbiology (1997), 143, 3193-3199; Ilkka M. Helander et al.; "Polyethyleneimine is an effective permeabilizer of Gram-Negative Bacteria".

XP-002394103—Derwent Abstract WPI Section Ch, Week 198904 (1989).

XP-002394104—Derwent Abstract WPI Section Ch, Week 199145 (1991).

BMC Biotechnology 2004, 4:23; Vancha A.R. et al.; "Use of polyethyleneimine polymer in cell culture as attachment facture and lipofection enhancer".

Chemguide excerpt, "Introducing Alcohols"; J.Clark; 2003, obtained from http://www.chemguide.co.uk/organicprops/alcohols/background_html on Mar. 21, 2010.

Office Action dated Mar. 29, 2010 in co-pending application (U.S. Appl. No. 11/638,745).

Final Rejection Office Action dated Oct. 14, 2010 in corresponding application U.S. Appl. No. 11/638,745.

BioTechnology and BioEngineering, vol. 83, No. 2, Jul. 20, 2003, pp. 168-172; Jian Lin et al.; "Mechanism of Bactericidal and Fungicidal Activities of Textiles Covalently Modified With Alkylated Polyethylenimine".

Macromol. Chem. Phys. 2005, 206, pp. 2160-2170; Ren-Hua Jin et al.; "Simple Synthesis of Hierarchically Structured Silicas by Poly(ethyleneimine) Aggregates Pre-Organized by Media Modulation".

French Search Report in co-pending application (FA676373) dated Aug. 10, 2006.

European Search Report dated Apr. 2, 2007 in corresponding foreign application EP 06291966.

European Search Report dated Jun. 5, 2007 in corresponding foreign application EP 06291966.

Journal of Bacteriology, vol. 185, No. 4, Feb. 2003, pp. 1316-1325, "Whole-Genome Sequence Variation among Multiple Isolates of *Pseudomonas aeruginosa*", Spencer, et al.

Database EMBL [Online], Dec. 23, 2002—EMBL: BZ559732—abstract, 2 pages, "pacs2-164_1792.x1 pacs2-164 *Pseudomonas aeruginosa* genomic clone pacs2-164_1792, DNA sequence." XP002436173.

Database EMBL [Online], Dec. 23, 2002—EMBL: BZ563551—abstract, 2 pages, "pacs2-164_4312.x1 pacs2-164 *Pseudomonas aeruginosa* genomic clone pacs2-164_4312, DNA sequence." XP002436174.

Office Action dated Aug. 23, 2011 in corresponding U.S. Appl. No. 11/638,745.

\* cited by examiner

SEQUENCE LISTING

```
<160> NUMBER OF SEQ ID NOS: 3

<210> SEQ ID NO 1
<211> LENGTH: 25
<212> TYPE: DNA
<213> ORGANISM: Pseudomonas aeruginosa
<220> FEATURE:
<221> NAME/KEY: primer_bind

<400> SEQUENCE: 1
tctaccgcgt cacttacgtg acacc                                        25

<210> SEQ ID NO 2
<211> LENGTH: 24
<212> TYPE: DNA
<213> ORGANISM: Pseudomonas aeruginosa
<220> FEATURE:
<221> NAME/KEY: primer_bind

<400> SEQUENCE: 2
```

```
cgaccagcca gagcttacgg agta                                      24

<210> SEQ ID NO 3
<211> LENGTH: 18
<212> TYPE: DNA
<213> ORGANISM: Pseudomonas aeruginosa
<220> FEATURE:
<221> NAME/KEY: primer_bind

<400> SEQUENCE: 3
cccgaggtgc tggtaact                                             18
```

METHOD FOR DETECTING MICROORGANISMS ON A MEMBRANE

This application is a Divisional of U.S. Ser. No. 11/638,745 filed Dec. 14, 2006, the disclosure of which is incorporated herein by reference.

BACKGROUND OF THE INVENTION

The present invention relates to a novel composition for permeabilizing microorganism walls and to the uses thereof, in particular the use thereof in a method for counting and/or for the targeted identification of the microorganisms in a liquid or gaseous medium.

The invention applies to the control of the microbiological quality of the liquid and gaseous media involved in production lines for food or pharmaceutical products.

In this field, the microorganisms to be detected are often present in very small number and it is advisable to distinguish the nature of the microbes in order to determine whether they present a risk to human health. The control carried out must warn of any contamination of the manufactured product within a short period of time, making it possible, where appropriate, to stop the manufacture thereof and to take decontamination steps.

Many methods have been developed in order to minimize the culturing time for microorganisms, while at the same time making it possible to search for certain microbes.

This is the subject in particular of the methods for detecting microorganisms carried out after filtration of the liquid through a membrane, described in application WO 01/59157. According to this method, the microorganisms contained in a liquid sample are retained at the surface of a membrane by passing the liquid through said membrane. The microorganisms are cultured at the surface of the membrane in contact with an agar culture medium for the amount of time necessary to form a microcolony not visible to the naked eye. The cells forming the microcolony are then lyzed in order to release their adenosine triphosphate (ATP) and nucleic acid content. The ATP is used as a marker for identifying and quantifying the live cells by ATP-bioluminescence. The detection is termed universal in that ATP is a marker that is present in all living microorganisms. Reading of the result is obtained by means of a chemiluminescence reaction involving the conversion of the ATP into photons by an enzyme specific for said ATP. The light signal is detected using an appropriate video interface (e.g.: LCD camera). The image obtained makes it possible to visualize in situ the site on the membrane where the microbe has developed, in a manner similar to conventional counting carried out on a Petri dish in agar medium.

The "Milliflex Rapid®" system, sold by the company Millipore, operates on the principle described above. It was designed in order to carry out the filtration and detection steps on one and the same membrane, which is maintained on a plastic support. This support is designed so as to fit onto the various devices that are used for the filtration, the culturing of the microorganisms, the impregnation of the membrane with detection reagents and the taking of images in a video chamber.

This miniaturized system allows an appreciable gain in time compared with the conventional tests on Petri dishes. Furthermore, it makes it possible to store the images obtained on a digital support, which makes it possible to monitor the contaminations (traceability).

However, this system has certain limits due to the fact that, in practice, the counting of the microorganisms present at the surface of the membrane is carried out after cell lysis. It is, consequently, difficult to reuse the same membrane with a view to accurately identifying the microorganisms detected.

However, in order to demonstrate the presence of certain microorganisms, it is possible to carry out a specific hybridization using labeled probes, whether they are nucleotide in nature or else of PNA (peptide nucleic acid) type.

PNA probes have the advantage of being peptide in nature, which makes it possible, in certain applications, to advantageously replace oligonucleotide probes.

In general, in situ probe hybridization requires complete accessibility to the nucleic acids of the cell otherwise this manipulation generates false negatives.

Application WO 2004/050902 describes a system of detection on a membrane which makes it possible to detect the presence of microorganisms contaminating blood samples.

The particularity of this system lies in the fact that the microorganisms are detected through the penetration of labeling agents into the microorganisms through their wall. The labeling agents used are small molecules, in particular compounds which intercalate nucleic acids (DNA, RNA), such as cyanin derivatives, propidium iodide, acridine orange or ethidium bromide, which poses less difficulty in terms of penetration into the microorganisms than oligonucleotide probes.

The liquid sample to be tested is diluted in a permeabilization solution comprising the labeling agent and a cell permeabilization reagent. The cells are incubated in this permeabilization solution, the aim of which is to increase the cell wall porosity, so as to facilitate the penetration of the labeling product into the microorganisms present. The permeabilization solution is subsequently filtered, with the possible microorganisms that it contains, through a membrane. The microorganisms present are then retained on the membrane, and are then detected by reacting the labeling agent with a compound and/or a light source which allows the emission of a fluorescent signal. This system has the advantage of not lyzing the microorganisms, or at least of limiting as much as possible their destruction before their detection.

This results in a detection that offers better resolution.

However, because the markers are not specific, this system does not make it possible to determine the nature of the microorganisms detected.

Furthermore, in such a system, the handling of the microorganisms takes place in solution, which requires specific precautions and equipment which is more complex. It should be noted that the incubation of the live cells in solution before filtration has the drawback that the cells can continue to grow and to divide before being fixed on the membrane, which casts some uncertainty on the final result of the test.

It is also difficult to suitably meter out the penetration reagent into a permeabilization solution according to the method described in WO 2004/050902, in particular when it is sought to simultaneously detect gram-positive bacteria, which are generally more sensitive to permeabilizing agents, and more resistant gram-negative bacteria.

The permeabilization agents which may go to make up the composition of the permeabilization solution are typically ethylenediaminetetraacetic acid (EDTA), polyethylene glycol (PEG), digitonin, nonensin, sodium hexamethaphosphate or benzalkonium chloride.

It is also possible to use polyethyleneimine (PEI), which is a slightly basic and polycationic aliphatic polymer known to make bacterial walls permeable to solutes, such as antibiotics, which do not normally penetrate into the cytoplasma bacteria [Helander, I. M. et al., Polyethyleneimine is an effective permeabilizer of gram-negative bacteria, Microbiology (1997), 143: 3193-3199].

The concentration of polyethyleneimine in the permeabilization solutions such as that described in WO 2004/050902 is limited to concentrations of generally less than 100 μg/ml. The concentration most suitable for gram-negative bacteria, such as *Esherichia coli*, is around 20-30 μg/ml.

SUMMARY OF THE INVENTION

The aim of the present invention is to find an answer to the limitations of the existing membrane detection systems mentioned above.

Surprisingly, the inventors have noted that the use of polyethyleneimine (PEI), combined with at least one alcohol, particularly a primary alcohol, and more particularly the ethanol, produces a more effective composition for permeabilizing microorganism walls. Such a composition makes it possible in particular to cause macromolecules, which are optionally labeled, such as nucleotide probes, to penetrate into microorganisms.

It has in particular become apparent that the microorganisms incubated in a composition comprising PEI and a primary alcohol, in particular ethanol, tolerate higher concentrations of PEI than in the compositions of the prior art. The combination with a primary alcohol makes it possible, in particular, to use PEI up to a concentration of between 100 and 1000 μg/ml without causing any marked cell lysis effect.

The term "microorganism" denotes, in the present invention, any (eukaryotic or prokaryotic) living cell, single-cell organism, gamete or virus comprising a genetic inheritance contained in an envelope formed by a single or multiple wall.

A composition as defined above allows macromolecules to penetrate into microorganisms while at the same time limiting the destruction of their walls.

A macromolecule is defined as a molecule resulting from the combination of a large number of simple molecules, such as polypeptides, proteins, glycoproteins, oligonucleotides, polysaccharides, nucleic acids (DNA, RNA), antibodies, or derivatives thereof.

Polyethyleneimine (PEI) is a soluble product available in several forms. The monomeric polymerized form, which has a molecular mass of approximately 750 kDa, is a preferred form according to the invention (CAS No. 9002-98-6). PEI is used in many fields, in particular as an agent for the flocculation of proteins and nucleic acids in solution in various purification methods. It is also used as a permeabilizing agent due to the fact that it has the property of reversibly destructuring the phospholipids present in cell walls, thus making these walls permeable to agents which are not normally allowed to penetrate into the cells.

A first subject of the invention is thus a composition for permeabilizing microorganism walls, comprising the combination of polyethyleneimine (PEI) with at least one alcohol, particularly a primary alcohol, most particularly ethanol.

Preferably, this composition does not comprise any detergents.

The concentration of PEI in the permeabilizing composition can be between 100 and 1000 μg/ml, preferably between 150 and 900 μg/ml, and more preferably between 200 and 800 μg/ml.

According to the invention, the primary alcohol is generally present in the permeabilizing composition at a concentration of between 5% and 95%, preferably between 5% and 50%, more preferably between 10% and 50%.

Another subject of the invention relates to the use of a composition according to the invention, and more particularly to a method for detecting microorganisms on a membrane, comprising a step consisting of the penetration of labeled macromolecules into the microorganisms.

For reasons which are not yet well known, the mixture of PEI with a primary alcohol, in particular ethanol, facilitates the penetration of macromolecules, such as nucleotide probes, into microorganisms.

Nucleotide probes which are preferred according to the invention allow specific hybridization of the ribosomal RNAs of microorganisms, in particular the 16S RNA or the 23S RNA of *Pseudomonas aeruginosa*. Such probes can in particular comprise a sequence corresponding to SEQ ID NO. 1, SEQ ID NO. 2 or SEQ ID NO. 3.

When these probes are capable of hybridizing with certain nucleic acids present in the microorganisms, said method makes it possible to specifically detect the type(s) of microorganisms present in the liquid or gaseous medium. The method results in a more accurate picture of the microbial population detected being obtained.

It is also possible to envisage that the macromolecules consist of antigens or antibodies and that they participate in a detection of the immunological type.

DETAILED DESCRIPTION OF THE INVENTION

A subject of the invention is more particularly the use of the permeabilizing composition as described above, in a method for counting and/or identifying, on a membrane, the microorganisms initially present in a liquid or gaseous medium.

According to one specific form of the invention, the method is characterized in that it comprises the following steps:

(a) the liquid or gaseous medium is filtered through a membrane so as to retain on or within the membrane the microorganisms present in this medium;

(b) the membrane and the microorganisms are brought into contact with a permeabilizing composition as described above, comprising polyethyleneimine and at least one alcohol;

(c) the cells are fixed to the membrane by means of a crosslinking agent;

(d) the microorganisms are brought into contact with one or more optionally labeled macromolecules capable of crossing the microorganism wall; and (e) detection of the macromolecules having penetrated into the microorganisms is carried out.

The microorganisms targeted by the method of the invention are more particularly chosen from gram-positive or gram-negative pathogenic bacteria of the genus *Pseudomonas, Escherichia, Legionella, Salmonella, Listeria, Bacillus, Streptococcus, Vibrio, Yersinia, Staphylococcus, Mycobacterium, Shigella, Clostridium, Campylobacter*, or *Aeromonas*; protozoa of the genus *Giardia, Entamoeba, Cryptosporidium* or *Cyclospora*; mycoplasmas of the genus *Mycoplasma* or *Ureaplasma*, fungi of the genus *Aspergillus, Candida* or *Penicillium*, and the hepatitis A and E viruses, which are microorganisms of pathogenic nature frequently encountered in the environment.

This method is, in principle, also applicable to the detection of unicellular algae such as cyanobacteria, unicellular forms of parasitic organisms such as amoebae or nematode, trematode or ascarid eggs, or else plant or animal gametes such as pollen or spermatozoa.

The aim of this method is to count the microorganisms present in a liquid medium such as water or a gaseous medium such as air, while at the same time determining, as far as possible, their identity (family, genus, species, etc.). The expression "liquid or gaseous medium" is intended to mean any fluid that can be filtered, by applying a difference in pressure, through a membrane having pores with an average diameter of generally between 0.1 and 1.5 microns, preferably between 0.15 and 0.8 microns, more preferably between 0.2 and 0.6 microns. Such a fluid may consist of pure solutions involved in the production of sterile products, but also of complex solutions (drinking water, serum, urine, amniotic fluid, etc.) or alternatively of gaseous mixtures such as atmospheric air.

The present method may, moreover, have applications in the fields of diagnosis for the analysis of samples originating from animals or patients.

The term "membrane" denotes, in the present application, a synthetic support having two faces, the pores of which have a known average diameter.

The membrane used in the context of the present invention generally exhibits a high surface/volume ratio and a constant thickness of preferably between 90 and 200 microns.

Such a membrane may be a monolayer or a multilayer membrane. In general, it consists of one or more materials chosen from polytetrafluoroethylene, poly(vinylidene fluoride) (PVDF), polycarbonate, polyamide, polyester, polyethersulfone, acetylcellulose and nitrocellulose.

The materials are preferably chosen so as to be compatible with the solvents used, in particular the alcohols and aldehydes that may be used at the various steps of the method.

The membrane on which the microorganisms are detected preferably consists mainly of PVDF (poly(vinylidene fluoride)) or of nylon. More preferably, it is a PVDF filter membrane, of the type such as that sold by the company Millipore under the trade name Milliflex and the references HVWP® or HVMFX®.

Step a) of the method according to the invention consists of the filtration of the liquid or gaseous medium to be analyzed through a membrane as defined above so as to retain at the surface of this membrane the microorganisms contained in said medium.

Once the microorganisms have been filtered and retained on the membrane, an optional step consisting of the culturing of the microorganisms in contact with an appropriate culture medium can be included in the method between steps a) and b). This culture medium is preferably an agar medium on which the membrane is placed after filtration. This step, which is optional, makes it possible to obtain colonies of each of the microorganisms initially filtered, in order to be able to more readily detect them.

According to the invention, the microorganisms are subsequently incubated in step b), in a permeabilizing composition according to the invention.

This incubation step is carried out in a small volume of solution that forms a film at the surface of the membrane. Advantageously, the permeabilizing composition can be contained in a solid support on which the membrane will be placed, such as, for example, an impregnated pad, which limits any possible movements of liquid at the surface of the membrane, and therefore the mixing of the microorganisms. It is carried out at a temperature of between 20° C. and 35° C. for a period of 5 to 20 minutes.

The method according to the invention is all the more effective since it comprises a step (c) by means of which the cells are fixed on the membrane by means of an agent that serves as a crosslinking agent.

This step makes it possible to fix the cells on the support constituted by the membrane. A preferred crosslinking agent according to the invention is chosen from glutaraldehyde, formaldehyde and paraformaldehyde, paraformaldehyde being defined as a molecule composed of at least six formaldehyde units. Advantageously, the fixing composition can be contained in a solid support on which the membrane will be placed, such as, for example, an impregnated pad, which limits any possible movements of liquid at the surface of the membrane, and thus the mixing of the microorganisms. Preferably, according to the invention, the fixing step is carried out at a temperature of between 20° C. and 35° C. for a period of from 5 to 20 minutes.

This fixing step can also be carried out by irradiation of the microorganisms on the membrane by means of UV radiation. The membrane then preferably consists of nylon.

Step d) consisting in bringing the microorganisms into contact with one or more optionally labeled macromolecules, which penetrate(s) through the microorganism wall into said microorganisms, is preferably carried out at the end of the respective incubation and fixing steps b) and c), since it is at this precise moment that it has been observed that the microorganism walls are the most permeable to macromolecules.

According to a preferred form of the invention, the macromolecules are labeled and used as probes.

The term "probe" is here intended to mean macromolecules capable of recognizing and of associating with a specific biological element of the microorganism, thus allowing it to be visualized.

According to yet another preferred form of the invention, the probe can be a macromolecule capable of hybridizing with DNA or RNA sequences present in the microorganism and exhibiting a certain degree of specificity with respect to said nucleic acids. Reference will then be made, in the present text, to nucleic acid probes. The invention envisages any type of nucleic acid probe known to those skilled in the art which can give rise to a hybridization with nucleic acids, such as, for example, simple oligonucleotides, oligonucleotides of 2'-O-methyl-RNA type, or probes of PNA type (probes consisting of a polypeptide chain substituted with purine and pyrimidine bases) [Nielsen P. E. et al. Science (1991) 254: 1497-1500] or LNA type (oligonucleotides comprising one or more 2'-O-4'-C-methylene-β-D-ribofuranosyl monomers) as described in patent EP 1 013 661.

According to a preferred aspect of the invention, the probes used for the purposes of the targeted detection of microorganisms such as *Pseudomonas aeruginosa* comprise one or more of the sequences indicated below:

5'-TCTACCGCGTCACTTACGTGACACC-3'        [SEQ ID No. 1]

5'-CGACCAGCCAGAGCTTACGGAGTA-3'         [SEQ ID No. 2]

5'-CCCGAGGTGCTGGTAACT-3'               [SEQ ID No. 3].

The sequences SEQ ID Nos. 1, 2 and 3 have the particularity of specifically and selectively hybridizing respectively to the 16S RNA or 23S RNA of *Pseudomonas aeruginosa*. The inventors have in fact noted that probes capable of hybridizing the ribosomal RNAs of microorganisms are particularly useful for carrying out the invention.

One aspect of the invention therefore consists of probes comprising a sequence corresponding to SEQ ID No. 1 or SEQ ID No. 2, i.e. a sequence exhibiting at least 80% identity, preferably 90%, more preferably 95%, with the sequences indicated above. Such probes are particularly indicated for carrying out a counting and/or identification method according to the invention. According to another aspect of the invention, the macromolecules which are made to penetrate into the microorganisms, and which may be of the same nature as the probes described above, are used as primers for carrying out an additional step consisting of the specific amplification of the nucleic acids contained in the microorganisms. If such macromolecules are used in the method according to the invention, then an additional, but nevertheless optional, step is introduced into the method between steps d) and e).

Such an amplification step can prove to be useful for optimal detection of the microorganisms by increasing the amount of the nucleic acids available for the purposes of the detection. If this amplification step is highly specific, it also makes it possible to identify the microorganisms with more selectivity and thus to decrease the number of false positives. The amplification is preferably an amplification of NASBA type [Compton, J., *Nature* (1991) 350: 91-92] or of LAMP-PCR type [Notomi T., *Nucleic Acids Research* (2000), 28(12): e63].

The probes or primers described above can be designed so as to detect just one or several types of microorganisms. They can, in this respect, exhibit a varying degree of specificity with respect to the biological elements present in the microorganisms. For example, if the primers or probes are nucleic acids chosen so as to hybridize with nucleic acids whose sequence is conserved in numerous species of microorganisms, the identification will not be very specific; if, on the other hand, their sequence is chosen so as to recognize only sequences specific to a small number of species, the specificity will be greater.

According to yet another specific form of the invention and advantageously, a step consisting of specific hybridization of the nucleic acid probes or of the primers with the nucleic acids of said microorganisms can be carried out after step d) and before the subsequent detection step e).

This step consisting of hybridization of the nucleic acid probes or primers is carried out under standard hybridization conditions known to those skilled in the art. It may also comprise a washing step for eliminating the nucleic acid probes or primers having given rise to nonspecific hybridizations.

For the purposes of the detection, the nucleic acid probes or primers according to the invention are preferably fluorescence-labeled or alternatively coupled to enzymes for carrying out a chemiluminescence reaction.

The microorganism detection step (e) is carried out by detecting the light signal originating from the chemiluminescence reaction or the emission obtained by fluorescence, corresponding to the labeling of the probe or of the primer, by means of an appropriate interface.

According to a more preferred aspect of the invention, the nucleic acid probes such as oligonucleotides are coupled to peroxidase. When peroxidase is brought into contact with luminol (peroxidase substrate), it degrades the latter and the degradation product emits photons which are detected by the video interface (LCD camera) of the Milliflex system.

According to yet another aspect, the invention consists of the use of a permeabilizing composition as described above, for carrying out a diagnostic test in vitro.

It is in fact possible to envisage using the specific properties of a permeabilizing composition according to the invention to cause nucleotide probes or any other molecular complex to penetrate into cells taken from humans or animals, or maintained in culture, in order to carry out in situ detection.

The permeabilizing composition according to the invention can also find many applications in the medical field, for example as a drug adjuvant for increasing the permeability of cell or microorganism walls, in order, for example, to sensitize said cells or said microorganisms to active ingredients such as antibiotics or antiviral agents.

More particularly, a composition according to the invention is useful for causing antisense nucleic acids, particularly antisense RNAs (RNAi) to penetrate into cells in which it is intended to inhibit the expression of certain genes, in particular in the treatment of genetic diseases or of certain cancers.

The present invention is also intended to cover a kit for detecting and counting the microorganisms in a liquid or gaseous medium, comprising at least:
  a membrane for filtering a liquid or gaseous medium; and
  a permeabilizing composition as described in the present invention.

Preferably, the membrane contained in this kit consists mainly of PVDF or of nylon.

Advantageously, such a kit also comprises a composition comprising a crosslinking agent chosen from glutaraldehyde, formaldehyde and paraformaldehyde. This second composition makes it possible to fix the microorganisms on the membrane, which makes it possible, by carrying out the method according to the invention, to obtain a better resolution of the detection.

A kit according to the invention can also comprise a probe for the specific detection of the microorganism being sought, in particular a probe as defined above comprising a sequence exhibiting at least 80% identity with SEQ ID No. 1, SEQ ID No. 2 or SEQ ID No. 3.

The aim of the following examples is to illustrate the invention.

EXAMPLE 1

Specific Detection of *P. aeruginosa* by Means of an Oligonucleotide Probe

Figure 1:
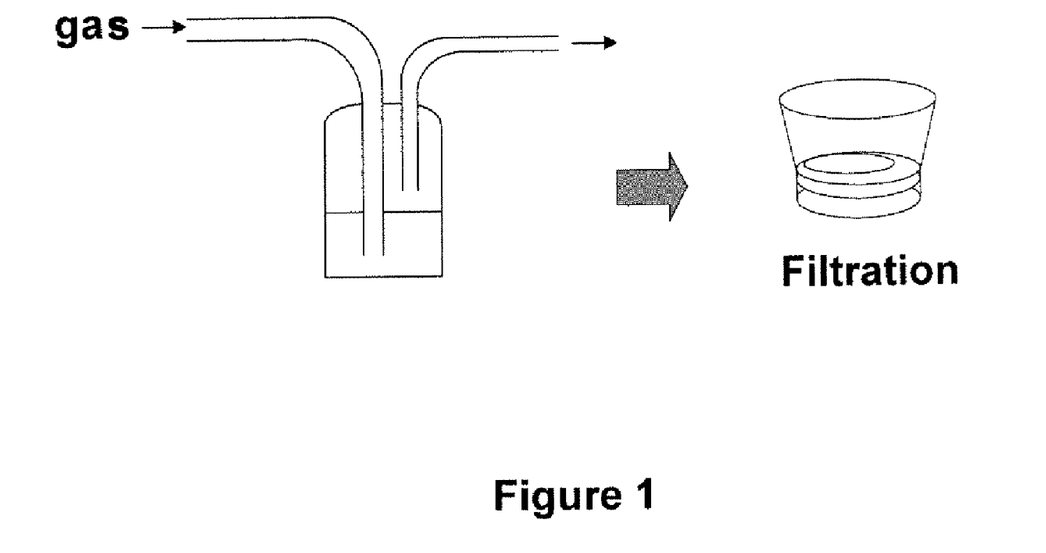
FIG. 1 indicates the way in which gaseous samples can be tested according to the method of the invention, by bubbling a gas or a gas mixture into a liquid such as 1% peptone water. Upon contact with the liquid, the microorganisms contained in the gas are trapped in the liquid. The liquid can then be filtered as indicated in the present application.
Figure 2:
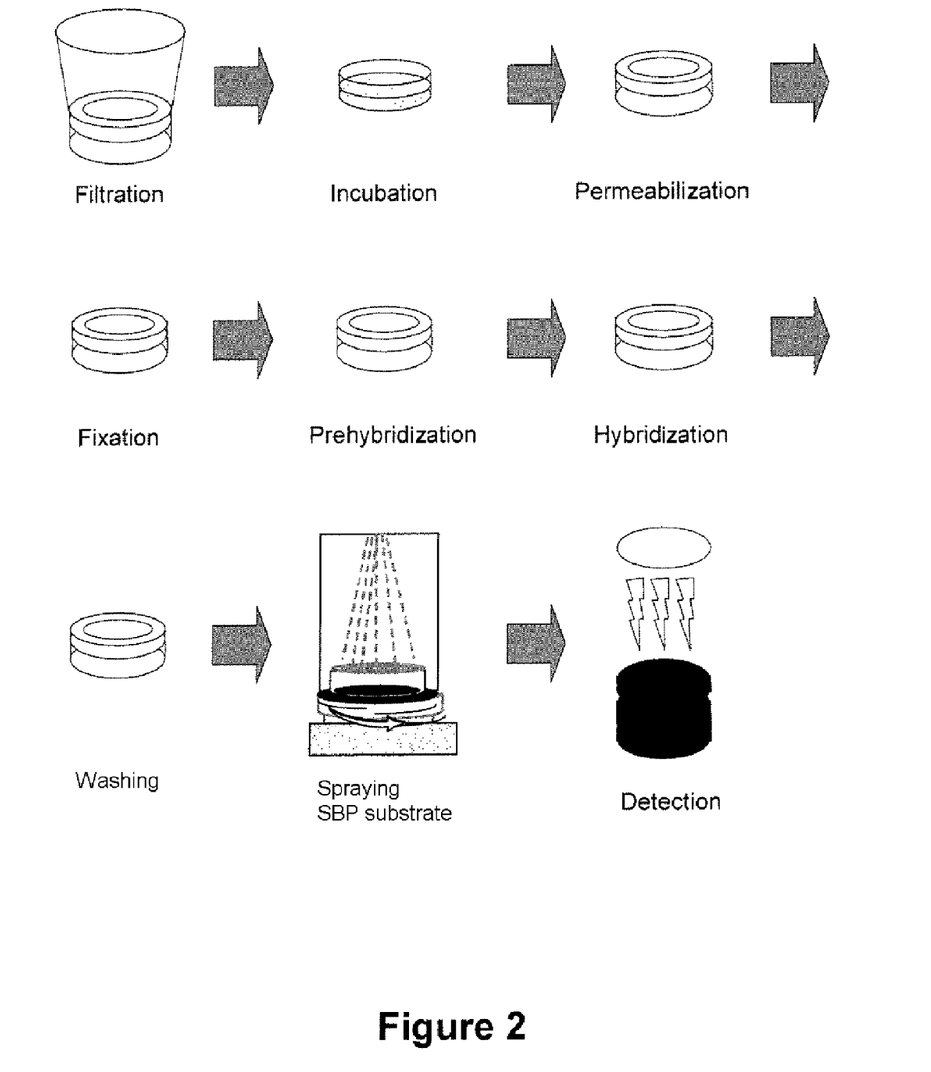
FIG. 2 illustrates the various steps of the method for detecting and counting microorganisms according to the invention carried out in example 1. The detection, carried out by means of a labeled oligonucleotide probe, is specific for *P. aeruginosa*.

The steps of the method which are carried out are illustrated in FIG. 2.

The implementation of this method consists first in filtering 100 ml of a solution using the device sold under the name Milliflex® with the reference HVWP® or HVMFX®. This device comprises a PVDF-type filter membrane held on a circular plastic structure.

Following the filtration, the membrane is placed on a cassette of agar medium and then incubated at 35° C. for 5 h 30 min so that the bacterial microcolonies can develop at the surface of the membrane.

The membrane is separated from the cassette of agar medium and then placed in contact with a cellulose pad impregnated with permeabilizing solution [20% ethanol, PEI 200 μg/ml] for 10 minutes at ambient temperature.

The membrane is then placed on a cellulose pad impregnated with the fixing solution [80% methanol, 1% formaldehyde, 5 mM $NaN_3$, 0.01% $H_2O_2$-urea] for 10 minutes at ambient temperature.

The plastic structure on which the membrane lies is subsequently fitted onto a hybridization cassette, the lower part of which is hermetically sealed. The membrane is incubated in the hybridization cassette at 45° C. for 30 minutes in contact with 2 ml of a first prehybridization solution [10% PEG; 300 mM NaCl; 30% formamide; 0.1% sodium pyrophosphate; 0.2% PVP; 0.2% Ficoll; 5 mM EDTA; 1% Triton X-100; 50 mM Tris-HCl—pH 7.5]. Once the first solution is removed, the membrane is placed in contact with the same volume of a hybridization solution containing 100 nM of an oligonucleotide probe coupled to soybean peroxidase at 45° C. for 60 minutes.

The oligonucleotide probe used, which is specific for the 16S RNA of *P. aeruginosa*, has the following sequence [SEQ ID No. 2]:

5'-CGACCAGCCAGAGCTTACGGAGTA-3' [SEQ ID No. 2].

The membrane is subsequently separated from the hybridization cassette and then placed in a washing tank in contact with 100 ml of a washing solution [10 mM CAPSO, 0.02% Tween20]. Three washes for 10 min at 45° C. are carried out.

The membrane is dried and then the bioluminescent reagent [Millipore cat #WBKLS0100], after reconstitution, is sprayed at the surface of the membrane. The device is placed in the Milliflex Rapid system and the light signals are recorded.

Figure 3:
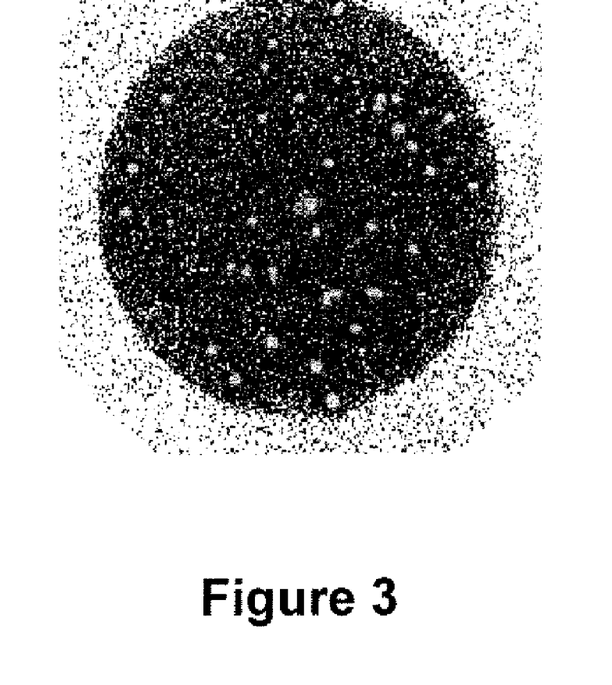
FIG. 3 represents the result of the test described in example 1. It is a representation of the membrane as a synthetic image, obtained after recording and digital processing of the light signals emitted by the probes.
Figure 4:
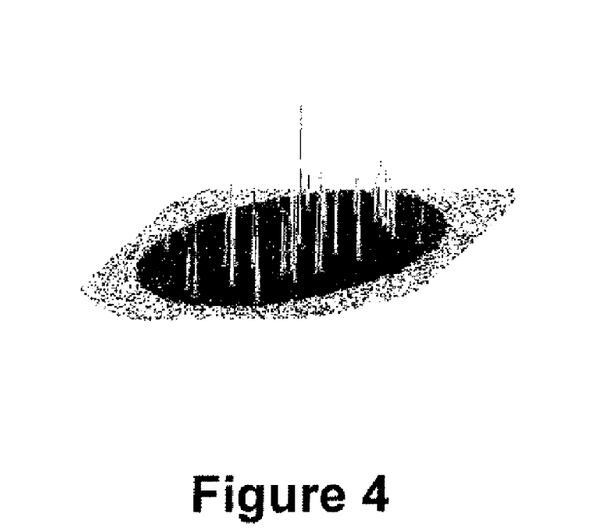
FIG. 4 is a three-dimensional representation of the image presented in FIG. 3.

The result of the detection of *P. aeruginosa* at the surface of the membrane is shown in FIG. 3. A three-dimensional view with the same analysis is shown in FIG. 4, where the membrane localization of each of the *P. aeruginosa* microcolonies is clearly distinguished.

EXAMPLE 2

Figure 5:
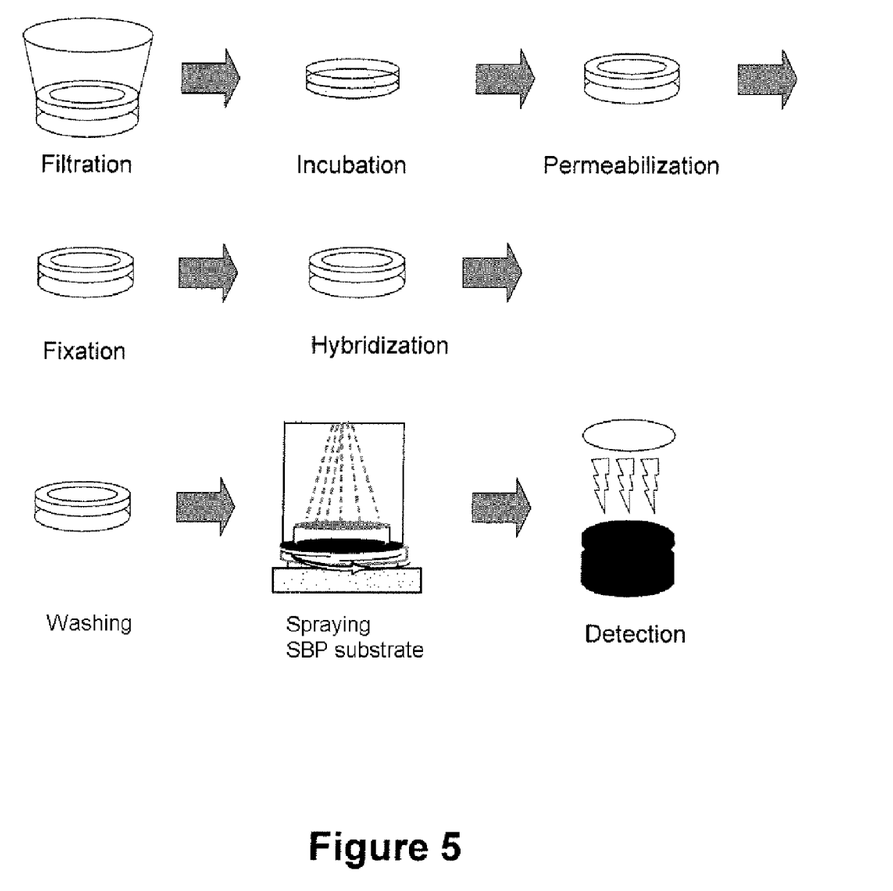
FIG. 5 illustrates the various steps of the method for detecting and counting microorganisms according to the invention carried out in example 2. The detection, carried out by means of a labeled PNA-type probe, is specific for *P. aeruginosa*.

Specific Detection of *P. aeruginosa* by Means of a PNA-Type Probe a) Use of a 20% Ethanol, PEI 200 μg/ml Permeabilizing Solution The steps of the method that are carried out are illustrated in FIG. 5.

After a filtration carried out according to the protocol of example 1, the membrane is placed on a cassette of agar medium and incubated at 35° C. for 6 h.

The membrane is separated from the cassette of agar medium and is then placed on a cellulose pad impregnated with the permeabilizing solution [20% ethanol, PEI 200 μg/ml] for 10 minutes at ambient temperature.

The device is subsequently placed on a cellulose pad impregnated with a fixing solution [80% methanol, 1% formaldehyde, 5 mM $NaN_3$, 0.01% $H_2O_2$-urea] for 10 minutes at ambient temperature.

The membrane is placed, as in example 1, on a hybridization cassette, in contact with 2 ml of a hybridization solution [10% PEG; 10 mM NaCl; 30% formamide; 0.1% sodium pyrophosphate; 0.2% PVP; 0.2% Ficoll; 5 mM EDTA; 1% Triton X-100; 50 mM Tris-HCl—pH 7.5] comprising 100 nM of a PNA probe coupled to soybean peroxidase. The assembly is placed at 50° C. for 60 minutes.

The PNA probe used is capable of hybridizing with the same 16S RNA sequence of *Pseudomonas aeruginosa* as the oligonucleotide probe of example 1, of sequence SEQ ID No. 3.

The membrane on its support is separated from the hybridization cassette and then placed in the washing tank in contact with 100 ml of a washing solution [10 mM CAPSO, 0.02% Tween20]. Three washes of 10 min at 50° C. are carried out.

Figure 6:
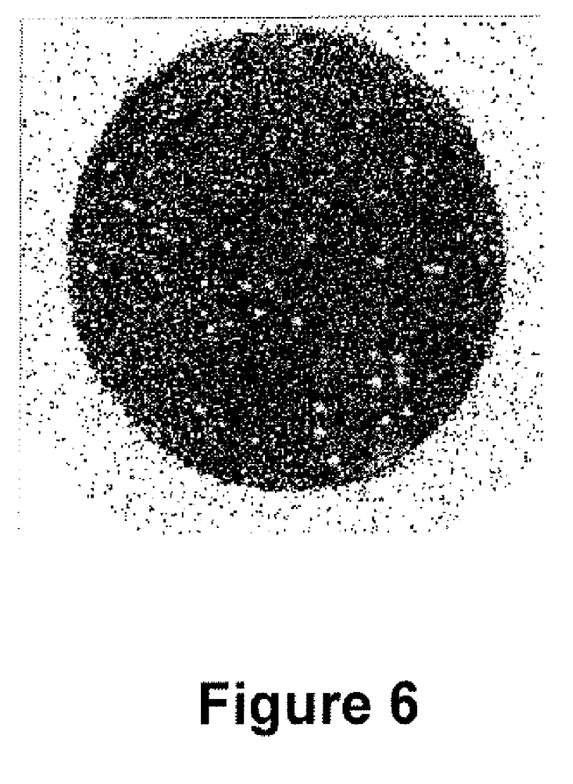
FIG. 6 represents the result of the test described in example 2. It is a representation of the membrane as a synthetic image, obtained after recording and digital processing of the light signals emitted by the probes.
Figure 7:
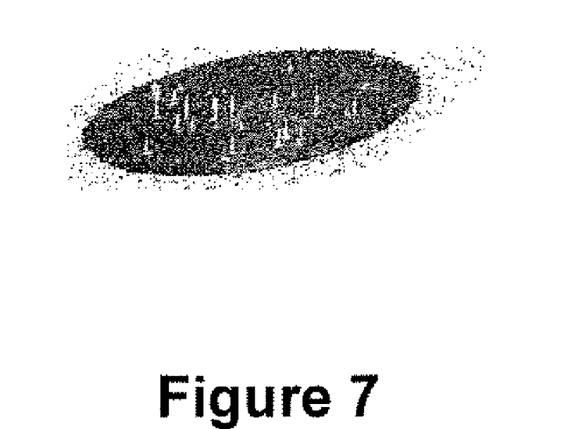
FIG. 7 is a three-dimensional representation of the image presented in FIG. 6.

The membrane is dried, and then the bioluminescent reagent [Millipore cat #WEKLS0100], after reconstitution, is sprayed at its surface. Finally, the membrane is placed in the image analyzer of the Milliflex Rapid system, where the light signals are recorded. The image obtained is shown in FIG. 6. A three-dimensional view of the same analysis is shown in FIG. 7.

This method makes it possible to specifically detect the presence of *P. aeruginosa* at the surface of a filter membrane.

b) Use of a permeabilization solution comprising 200 μg/ml of PEI alone, 500 μg/ml of PEI alone or a mixture composed of 10% ethanol and PEI at a concentration of 500 μg/ml (EtOH 10%-PEI500)

The same protocol as that described above was carried out with a permeabilizing solution comprising only PEI, and then with a mixture composed of 10% ethanol and PEI at a concentration of 500 μg/ml (EtOH10%—PEI500).

Following the filtration, the membrane was placed on a cassette of agar medium and then incubated at 35° C. for 15 h.

The membrane was subsequently placed on a cellulose pad impregnated with a permeabilizing solution containing 200 μg/ml of PEI alone, 500 μg/ml of PEI alone, or a mixture composed of 10% ethanol and PEI at a concentration of 500 μg/ml, for 10 minutes at ambient temperature, a nontreated membrane having been used as a control.

The membrane was subsequently placed on a cellulose pad impregnated with the fixing solution [80% methanol, 1% formaldehyde, 5 mM $NaN_3$, 0.01% $H_2O_2$-urea] for 10 minutes at ambient temperature, and then treated as indicated above.

Figure 9:
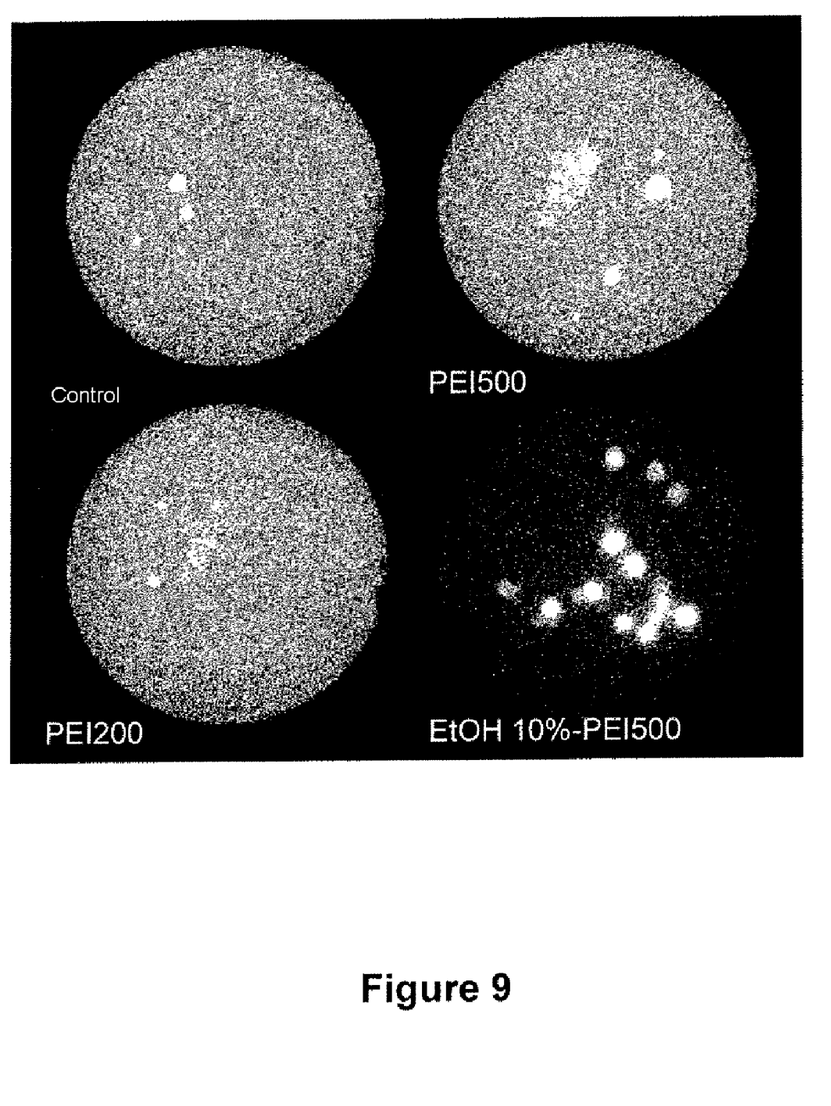
FIG. 9 represents the result of the test carried out in example 3b) comparing various permeabilizing solutions (PEI200 μg/ml, PEI500 μg/ml and 10% ethanol+PEI500 μg/ml). These are the synthetic images obtained after recording and digital processing of the light signals emitted by ATP-bioluminescence.

The results obtained for the various concentrations of PEI, and also for the joint use of PEI and alcohol, are shown in FIG. 9.

It can be noted therein that the joint use of PEI and EtOH makes it possible to obtain a strong and precise signal by comparison with that which can be obtained in the absence of permeabilizing agent (control) or in the presence of PEI alone.

EXAMPLE 3

Nonspecific Detection of Microorganisms by ATP-Bioluminescence

The permeabilizing composition according to the invention can be used in a method for detecting the ATP produced by living microorganisms, according to a chemibioluminescence reaction known from the prior art [Alexander, D. N., G. M. Ederer, and J. M. Matsen. 1976. Evaluation of an adenosine 5'-triphosphate assay as a screening method to detect significant acteriuria. *J. Clin. Microbiol.* 3:42-46].

Figure 8:
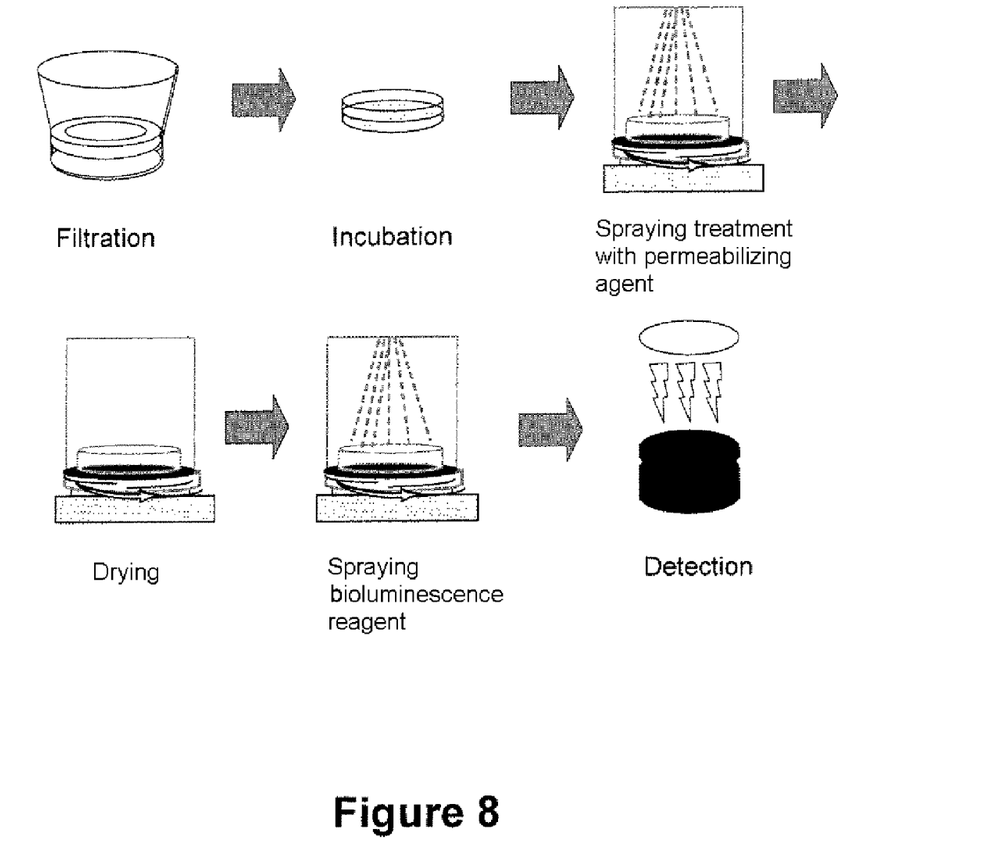
FIG. 8 illustrates the various steps of the method for detecting microorganisms by ATP-bioluminescence carried out in example 3.

The use of a composition according to the invention makes it possible to obtain better permeabilization of the wall of microorganisms with a view to releasing their ATP content.

a) Treatment of Cells with 90% Ethanol or 25% Ethanol-PEI 500 µg/ml Before Detection of ATP by Chemiluminescence A method for detecting *Saccharomyces cerevisiae* present in water, by ATP-bioluminescence, in which the various steps are illustrated in FIG. 8, was tested. In this test, the cells are pretreated with 90% ethanol or with 25% ethanol-PEI 500 µg/ml, before the chemiluminescence reaction.

The protocol consists, as in the preceding examples, in filtering 100 ml of a solution using the Milliflex® device.

The membrane is then treated with 40 µl of a solution of 90% ethanol or of 25% ethanol-PEI 500 µg/ml which is sprayed at the surface of the membrane, and then again dried.

The membrane is subsequently treated with 40 µl of a bioluminescence solution sprayed at the surface of the membrane, and then placed in the image analyzer where the light signals are recorded.

b) Treatment with PEI Alone (100-500 µg/ml) or with Ethanol-PEI Mixtures Before Detection of ATP by Chemiluminescence The same protocol as described above was carried out, in which the treatment with ethanol was replaced with a treatment with PEI alone (100-250-500 µg/ml) or with mixtures of ethanol-PEI (composition according to the invention): EtOH 10%—PEI100 µg/ml; EtOH 10%—PEI250 µg/ml; EtOH 10%—PEI500 µg/ml EtOH.

Figure 10:
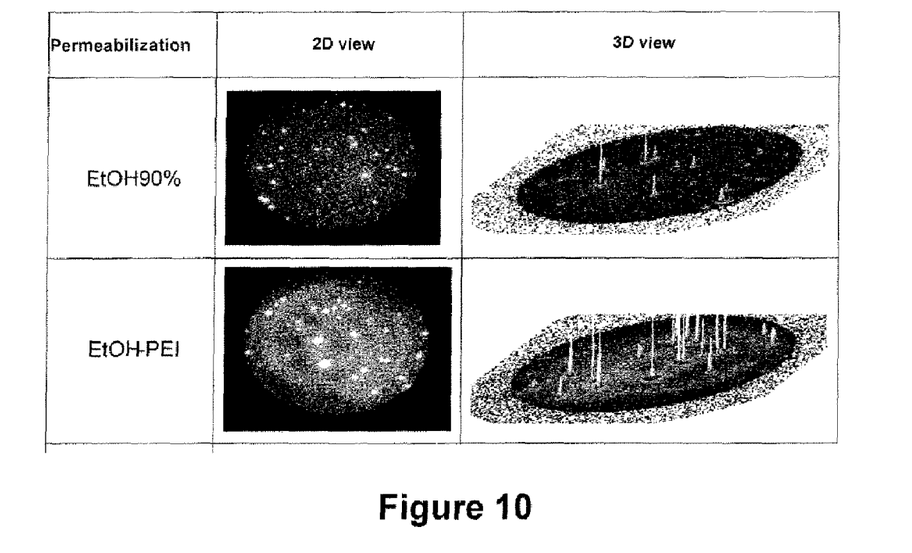
FIG. 10 represents the same thing as in FIG. 9 for other permeabilizing solutions (90% ethanol and 25% ethanol+PEI500 μg/ml).
Figure 11:
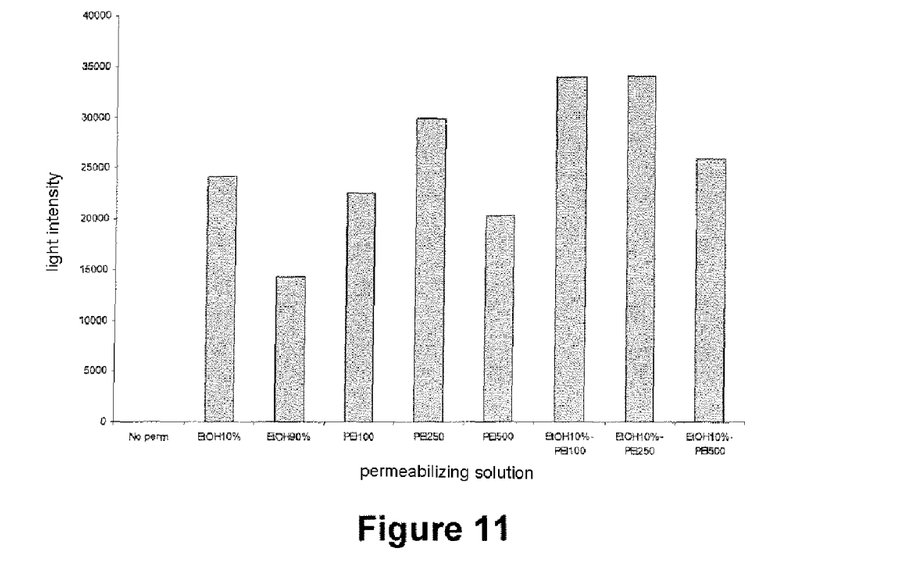
FIG. 11 is a diagram indicating the light intensity measured for each permeabilizing solution tested in the context of the ATP-bioluminescence protocol illustrated in FIG. 8.

The results concerning the various treatments according to a) and b) are shown in the table of FIG. 10 and in the diagram of FIG. 11. It emerges from these comparative results that the combination of EtOH and PEI makes it possible to obtain a signal which is clearly stronger than with the use of EtOH alone or PEI alone, even when the PEI alone is used at high concentrations.

EXAMPLE 4

Nonspecific Detection of Microorganisms by Penetration of a DNA-Intercalating Agent (SYBRgreen)

One experiment consisted in incubating *E. coli* bacteria in solution in a composition according to the invention comprising a 10% ethanol-PEI 100 µg/ml mixture.

The same experiment was carried out by incubating the cells in a solution of PEI alone at a concentration of 25 µg/ml or of 100 µg/ml, or in the absence of permeabilization (PBS).

The experiment consisted in incubating the bacteria for 15 minutes in the presence of the abovementioned agents and of a DNA-intercalating agent (SYBRgreen I, 1/4000) and then in measuring the presence of fluorescence using a microplate reader.

The results are reported in table 1 shown below.

The combination of EtOH and PEI makes it possible to obtain a signal which is clearly stronger than when the PEI is used alone. This shows that better microorganism wall permeability can be obtained by combining the alcohol with PEI.

TABLE 1

| Permeabilization and labeling of *E. coli* (SYBRgreen) | |
| --- | --- |
| Permeabilizing solution | Fluorescence Relative fluorescence units (*E. coli*) |
| PBS | 9375 |
| PEI 25 µg/ml | 13036 |
| PEI 100 µg/ml | 15152 |
| PEI 100 µg/ml/EtOH10% | 20998 |

The invention claimed is:

1. Method for counting and/or identifying on a membrane gram-negative bacteria initially present in a liquid or gaseous medium, comprising the following steps: (a) filtering said liquid or gaseous medium through a membrane so as to retain on or within the membrane the bacteria present in this medium; (b) contacting said membrane and said bacteria with a permeabilizing composition comprising polyethyleneimine and ethanol; (c) fixing said bacteria to the membrane by means of a crosslinking agent; (d) contacting said bacteria with one or more macromolecules capable of crossing the bacterial walls of gram-negative bacteria fixed to the membrane in step (c), said macromolecules being labeled with a member selected from the group consisting of an enzyme that allows the emission of a light signal and a fluorescent molecule; (e) hybridizing said one or more macromolecules with the nucleic acids of said gram-negative bacteria; (f) detecting the one or more macromolecules having penetrated into said gram-negative bacteria by causing a light signal or fluorescence signal to be generated and detecting said signal; and (g) counting and/or identifying the gram-negative bacteria initially present in said liquid or gaseous medium.

2. Method according to claim 1, further comprising, between step a) and step b), an additional step consisting of the culturing of said gram-negative bacteria.

3. Method according to claim 1, wherein said crosslinking agent in step c) is selected from the group consisting of glutaraldehyde, formaldehyde and paraformaldehyde.

4. Method according to claim 1, wherein in step d), the one or more macromolecules is a PNA-type probe.

5. Method according to claim 4, wherein the probe used in step d) comprises a sequence exhibiting at least 80% identity with SEQ ID No. 1, SEQ ID No. 2 or SEQ ID No. 3.

6. Method according to claim 5, wherein the membrane is selected from the group consisting of PVDF and Nylon®.

7. Method according to claim 1, wherein in step d), the one or more macromolecules is an oligonucleotide-type probe.

8. Method according to claim 1, wherein said one or more macromolecules comprise probes or primers, and wherein in step d), the probes or the primers are labeled by coupling with an enzyme that allows the emission of a light signal.

9. Method according to claim 8, wherein the detection of the one or more macromolecules in step (f) is carried out by means of a chemiluminescence reaction and recognition of the light signal emitted by means of a video interface.

10. Method according to claim 1, wherein said one or more macromolecules comprise probes or primers, and wherein in step d), the probes or the primers are labeled with a fluorescent molecule.

11. Method according to claim 10, wherein the detection of the macromolecules in step (f) is carried out by detecting a fluorescence emission signal, corresponding to the labeling of the probes or of the primers, by means of a video interface.

12. Method according to claim 1, further comprising, between step d) and step e), an additional step consisting of amplification of nucleic acids present in said gram-negative bacteria.

* * * * *